United States Patent
Linder et al.

(10) Patent No.: US 7,351,723 B2
(45) Date of Patent: *Apr. 1, 2008

(54) FREEZE-DRIED PANTOPRAZOLE PREPARATION AND PANTOPRAZOLE INJECTION

(75) Inventors: Rudolf Linder, Constance (DE); Rango Dietrich, Constance (DE)

(73) Assignee: Nycomed GmbH, Constance (DE)

( * ) Notice: Subject to any disclaimer, the term of this patent is extended or adjusted under 35 U.S.C. 154(b) by 42 days.

This patent is subject to a terminal disclaimer.

(21) Appl. No.: 10/855,703

(22) Filed: May 28, 2004

(65) Prior Publication Data

US 2004/0220228 A1    Nov. 4, 2004

Related U.S. Application Data

(63) Continuation of application No. 10/195,062, filed on Jul. 15, 2002, which is a continuation-in-part of application No. PCT/EP01/13296, filed on Nov. 17, 2001, now Pat. No. 6,780,881.

(30) Foreign Application Priority Data

Nov. 22, 2000 (EP) .................................. 00125569

(51) Int. Cl.
*A61K 31/44* (2006.01)
*A61K 31/41* (2006.01)

(52) U.S. Cl. ..................... 514/338; 514/926; 514/927

(58) Field of Classification Search ............... 514/338, 514/925, 926, 927, 359, 360; 424/46; 548/304.4
See application file for complete search history.

(56) References Cited

U.S. PATENT DOCUMENTS 4,758,579 A    7/1988  Kohl et al.
5,589,491 A    12/1996 Nakanishi et al.
5,980,882 A *  11/1999 Eichman ................. 424/78.12
6,730,685 B1   5/2004  Brülls
6,780,881 B2 * 8/2004  Linder et al. ............ 514/338
6,923,988 B2 * 8/2005  Patel et al. .............. 424/489
2003/0003058 A1 1/2003 Linder et al.

FOREIGN PATENT DOCUMENTS

| CN | 1235018 | * | 11/1999 |
| CN | 11235018 | | 11/1999 |
| DE | 43 24 014 | | 1/1995 |
| DE | 4324014 | * | 1/1995 |
| EP | 0 124 495 B1 | | 11/1984 |
| EP | 0 356 143 B1 | | 2/1990 |
| WO | WO 94/02141 | | 2/1994 |
| WO | WO 00/10995 | * | 8/1998 |
| WO | WO 99/18959 | | 4/1999 |

OTHER PUBLICATIONS

RxList: Insulin (Human Recombinant); retrieved on Apr. 3, 2006 from the internet http://rxlist.com/cgi/generic/insuhumr_pi.htm.*
"A polyclonal antibody to protein disulfide isomerase induces platelet aggregation and secretion", Essex, DW, et al., Thromb. Res. Dec. 15, 1999; 96(6):445-50.
Physician's Desk Reference, PDR Entry for Protonix I.V. (Wyeth-Ayerst), vol. 58 (2004), pp. 3480-3483.
BASF-Pharma UK, *Summary of Product Characteristics*, (Section 3), "Protium i.v. pantoprazole sodium lyophile", Jan. 2000.
Kibbe, A.H. "Handbook of Pharmaceutical Excipients", Pharmaceutical Press, pp. 191-194, 649 (2000).

* cited by examiner

*Primary Examiner*—Ardin H. Marschel
*Assistant Examiner*—Zohreh Vakili
(74) *Attorney, Agent, or Firm*—The Nath Law Group; Joshua B. Goldberg; Sheldon M. McGee

(57) ABSTRACT

Lyophilized pantoprazole preparations which are obtainable by freeze-drying of an aqueous solution of pantoprazole, ethylenediamine tetraacetic acid and/or a suitable salt thereof, and sodium hydroxide and/or sodium carbonate are disclosed. The preparations have advantageous properties when reconstituted for injection.

14 Claims, No Drawings

FREEZE-DRIED PANTOPRAZOLE PREPARATION AND PANTOPRAZOLE INJECTION

This application is a Continuation of USSN 10/195,062, filed Jul. 15, 2002, now U.S. Pat. No. 6,780,831, which is a Continuation-In-Part (CIP) of International Patent Application No. PCT/EP01/13296 filed Nov. 17, 2001.

TECHNICAL FIELD

The present invention relates to the field of pharmaceutical technology and describes freeze-dried 5-difluoromethoxy-2-[(3,4-dimethoxy-2-pyridinyl)methylsulfinyl]-1H-benzimidazole preparations and a 5-difluoromethoxy-2-[(3,4-dimethoxy-2-pyridinyl)methylsulfinyl]-1H-benzimidazole injection. Furthermore the invention also relates to a process for the production of freeze-dried 5-difluoromethoxy-2-[(3,4dimethoxy-2-pyridinyl)methylsulfinyl]-1H-benzimidazole and a 5-difluoromethoxy-2-[(3,4-dimethoxy-2-pyridinyl)methylsulfinyl]-1H-benzimidazole injection.

PRIOR ART

WO94/02141 describes an injection comprising a 2-[(2-pyridyl)methylsulfinyl]-benzimidazole compound an aqueous solvent added with no nonaqueous solvent, wherein the pH of the injection is not less than 9.5 and not more than 11.5. It is mentioned that said injection does not cause hemolysis and causes less local irritation.

DE 43 24 014 describes the preparation of a lyophilisate of pantoprazole-sodium sesquihydrate in the presence of sucrose as an auxiliary at production temperatures of −25 to −30° C. It is disclosed that the lyophilisate is of improved storage stability and can be stored at room temperature for at least 18 months and is easily reconstituted in liquid form in suitable doses for use.

CN 1235018 describes a freeze-dried injection powder of pantoprazole sodium containing no crystallised water with pH value of 9-12.5, which is composed of pantoprazole sodium, freeze-dried powder supporting agent, metal ion complexing agent and pH regulator.

WO99/18959 describes aqueous pharmaceutical compositions which are chemically and physically stable for intravenous injection which comprise anti-ulcerative compound and glycine as stabilizer in carrier.

DESCRIPTION OF INVENTION

Reconstitution of lyophilised pharmaceutical compounds with carrier solutions for application may lead to the formation of visible and/or subvisible particles in the solution. Injectable solutions, including solutions constituted from sterile solids intended for parenteral use should be essentially free from particles that can be observed on visual inspection and for patient safety it is also desirable to have a low number of subvisible particles. USP (United States Pharmacopeia) 24 describes physical tests performed for the purpose of enumerating subvisible extraneous particles within specific size ranges and also defines particulate matters limits set forth for the test being applied for large-volume injections for single-dose infusion and small-volume injections (USP 24, <788> Particulate Matter in injections).

Surprisingly it has now been found that by freeze drying of an aqueous solution of pantoprazole, ethyl-enediamine tetraacetic acid and/or a suitable salt thereof, and sodium hydroxide and/or sodium carbonate a lyophilisate is obtained having significantly lower number of subvisible particles after reconstitution with a solvent compared to lyophilisates of the state of the art. The lyophilisate according to the invention is very stabile and is easily reconstituted with suitable solvents. In particular the pantoprazole injection according to the invention has less than 130, preferably less than 120 subvisible particles/per vial, the particles having a size equal to or greater as 10 µm, the number of particles determined according to USP 24 (<788> Particle Matter in injections) by light obscuration particle test count.

5-Difluoromethoxy-2-[(3,4-dimethoxy-2-pyridinyl)methylsulfinyl]-1H-benzimidazole (INN: pantoprazole, in connection with the invention also referred to as pantoprazole) is known from EP-A-0 166 287. Pantoprazole is a chiral compound. In connection with the invention the term pantoprazole also includes the pure enantiomers of pantoprazole and their mixtures in any mixing ratio. (S)-pantoprazole [(−)-pantoprazole] may be mentioned by way of example. Pantoprazole is present here as such or preferably in the form of it's salt with a base. Examples of salts with a base which may be mentioned are sodium, potassium, magnesium and calcium salts. Pantoprazole and/or a salt thereof may contain various amounts of solvent when isolated in crystalline form. In connection with the invention pantoprazole also refers to all solvates and in particular to hydrates of 5-difluoromethoxy-2-[(3,4-dimethoxy-2-pyridinyl) methylsulfinyl]-1H-benzimidazole and salts thereof. Such a hydrate of the salt of pantoprazole with a base is disclosed, for example, in WO91/19710. Expediently pantoprazole refers to pantoprazole sodium sesquihydrate (=pantoprazole sodium×1.5H$_2$O) and pantoprazole magnesium dihydrate.

According to the, invention the pantoprazole solution used in the freeze drying process can be obtained by addition of ethylenediamine tetraacetic acid and/or a suitable salt thereof, and sodium hydroxide and/or sodium carbonate to an aqueous solvent. Suitable salts of ethylenediamine tetraacetic acid which may be mentioned in connection with the invention by way of example are ethylenediamine tetraacetic acid disodium salt, ethylenediamine tetraacetic acid calcium disodium salt ethylenediamine tetraacetic acid trisodium salt and ethylenediamine tetraacetic acid tetrasodium salt. The proportion by weight of ethylenediamine tetraacetic acid and/or a suitable salt thereof, based on the amount of pantoprazole used is from 0.05 to 25% preferably from 0.25 to 12.5% or particular preferred from 1 to 5%. The aqueous solvent preferentially is water for injection. Subsequently pantoprazole is added to the solution and dissolved by stirring. It is preferred to have a solution wherein the proportion of weight (m/m) of pantoprazole is 0.5 to 10%, particularly preferred 1 to 6%. In a further preferred embodiment of the invention the pH of the solution used in the freeze drying process is 8 or above 8. Particularly preferred the pH of said solution is in the range from 10 to 13, more preferred the pH of the solution is in the range from 10.5 to 11.5 and particularly more preferred the pH is in the range from 10.75 to 11.25. Exemplary pH values of said solution, which are to be emphasized are 10.75, 10.8, 10.85, 10.9, 10.95, 11, 11.05, 11.1, 11.15, 11.2 and 11.25. Then this solution is filtered for sterilization and charged in vials. The solution is then freeze dried by a method known per se.

A pantoprazole injection according to the invention can be produced by dissolving the lyophilized product thus obtained in a suitable solvent for example physiological saline, aqueous solution of 5% glucose, or distilled water for injection. Preferably the pantoprazole injection according to the invention is used in the form of intravenous injection.

The lyophilised product and pantoprazole injection according to the invention preferably contain pantoprazole in the dose customary for the treatment of the respective disease. The lyophilised product and pantoprazole injection according to the invention can be employed for the treatment and prevention of all the diseases which are regarded as treatable or avoidable by the use of pyridin-2-ylmethylsulfinyl-1H-benzimidazoles. In particular, the lyophilised product and pantoprazole injection according to the invention can be employed in the treatment of stomach disorders. The lyophilized products in particular contain between 5 and 150 mg, preferably between 5 and 60 mg, of pantoprazole. Examples which may be mentioned are lyophilized products or injections which contain 10, 20, 40, 50 or 96 mg of pantoprazole. The administration of the daily dose (e.g. 40 mg of active compound) can be carried out, for example, in the form of an individual dose or by means of a number of doses of the administration forms according to the invention (e.g. 2 times 20 mg of active compound). The concentration of pantoprazole in the injection according to the invention may vary depending upon the administration route and generally ranges in a proportion of 0.05-10 mg/ml, preferably 0.1 to 5 mg/ml on a free compound basis. For example for bolus administration 20 to 120 mg of lyophilized product according to the invention can be reconstituted with 10 ml physiological saline.

The production of the lyophilized product and pantoprazole injection is described by way of example below. The following examples illustrate the invention in greater detail, without restricting it.

EXAMPLES

Production of a Lyophilized Pantoprazole Preparation

Example 1

Under nitrogen atmosphere, 0.276 g Ethylenediamine tetraacetic acid disodium salt and 6.7 g sodium hydroxide (1N aqueous solution) are added to 480 g water for injection of 4° C. To 8° C. 12.47 g pantoprazole sodium sesquihydrate is added while stirring to give a clear solution. The weight of the solution is adjusted to 500 g by addition of water for injection. The pH of the solution is 11.76. The solution is filtered through a 0.2 μm membrane filter and filled in glass vials (1.81 g by vial). Filled vials are semi-stoppered and put into a freeze-dryer (GT4 Edwards/Kniese or GT8 Amsco) for lyophilisation. The vials are cooled to −45° C., then the temperature is raised to −20 to −5° C. under vacuum (0.1 to 0.5 mbar) for drying. After finishing main drying the temperature is raised to 30° C., the vacuum is adjusted to 0.01 mbar and drying is continued for an additional 3 hours. An off-white lyophilized product is obtained which is easily reconstituted with physiological saline to give a clear solution.

Example 1a

Under nitrogen atmosphere, 0.276 g Ethylenediamine tetraacetic acid disodium salt and 1.66 ml sodium hydroxide solution (1N aqueous solution) are added to 480 g water for injection of 4° C. To 8° C. 12.47 g pantoprazole sodium sesquihydrate is added while stirring to give a clear solution. The weight of the solution is adjusted to 500 g by addition of water for injection. The pH of the solution is 11.76. The solution is filtered through a 0.2 μm membrane filter and filled in glass vials (1.81 g by vial). Filled vials are semi-stoppered and put into a freeze-dryer (GT4 Edwards/Kniese or GT8 Amsco) for lyophilisation. The vials are cooled to −45° C. then the temperature is raised to −20 to −5° C. under vacuum (0.1 to 0.5 mbar) for drying. After finishing main drying the temperature is raised to 30° C., the vacuum is adjusted to 0.01 mbar and drying is continued for an additional 3 hours. An off-white lyophilized product is obtained which is easily reconstituted with physiological saline to give a clear solution.

Comparative Examples

Example 2

Under nitrogen atmosphere, 12.47 g pantoprazole sodium sesquihydrate is added to 480 g water for injection of 4° C. To 8° C. while stirring to give a clear solution. The volume of the solution is adjusted to 500 g by addition of water for injection. The pH of the solution is 10.85. The solution is filtered through a 0.2 μm membrane filter and filled in glass vials (1.81 g by vial). Filled vials are semi-stoppered and put into a freeze-dryer (GT4 Edwards/Kniese or GT8 Amsco) for lyophilisation. The vials are cooled to −45° C., then the temperature is raised to −20 to −5° C. under vacuum (0.1 to 0.5 mbar) for drying. After finishing main drying the temperature is raised to 30° C., the vacuum is adjusted to 0.01 mbar and drying is continued for an additional 3 hours. An off-white lyophilized product is obtained.

Example 3

Under nitrogen atmosphere, 2.45 g sodium hydroxide (1N aqueous solution) is added to 480 g water for injection of 4° C. To 8° C. 12.47 g pantoprazole sodium sesquihydrate is added while stirring to give a clear solution. The weight of the solution is adjusted to 500 g by addition of water for injection. The pH of the solution is 12.02. The solution is filtered through a 0.2 μm membrane filter and filled in glass vials (1.81 g by vial). Filled vials are semi-stoppered and put into a freeze-dryer (GT4 Edwards/Kniese or GT8 Amsco) for lyophilisation. The vials are cooled to −45° C., then the temperature is raised to −20 to −5° C. under vacuum (0.1 to 0.5 mbar) for drying. After finishing main drying the temperature is raised to 30° C., the vacuum is adjusted to 0.01 mbar and drying is continued for an additional 3 hours. An off-white lyophilized product is obtained.

Example 4

Under nitrogen atmosphere, 0.05 g Ethylenediamine tetraacetic acid disodium salt is added to 480 g water for injection of 4° C. To 8° C. 12.47 g pantoprazole sodium sesquihydrate is added while stirring to give a clear solution. The weight of the solution is adjusted to 500 g by addition of water for injection. The pH of the solution is 10.2. The solution is filtered through a 0.2 μm membrane filter and filled in glass vials (1.81 g by vial). Filled vials are semi-stoppered and put into a freeze-dryer (GT4 Edwards/Kniese or GT8 Amsco) for lyophilisation. The vials are cooled to −45° C., then the temperature is raised to −20 to −5° C. under vacuum (0.1 to 0.5 mbar) for drying. After finishing main drying the temperature is raised to 30° C. the vacuum is adjusted to 0.01 mbar and drying is continued for an additional 3 hours. An off-white lyophilized product is obtained.

Light Obscuration Particle Test Count

Particulate matter/per vial in solutions constituted from the lyophilized products obtained according to Examples 1 to 4 were determined according to USP 24 (<788>Particulate Matter in injections) by light obscuration particle test count.

The number of extraneous particles per vial having a size equal to or greater as 10 μm detected are summarized in Table 1. As may be evident from table 1, the number of subvisible particles per vial (equal to or greater as 10 μm) in solutions constituted from products obtained according to the invention (EXAMPLE 1) is lower than for products obtained by methods which differ from the present invention (EXAMPLES 2 to 4).

TABLE 1

| EXAMPLE 1 (Product obtained by freeze drying of Pantoprazole sodium sesquihydrate, sodium hydroxide and ethylenediamine tetraacetic acid disodium salt) particles/per vial $>= 10$ μm | EXAMPLE 2 (Product obtained by freeze drying of Pantoprazole sodium sesquihydrate) particles/per vial $>= 10$ μm | EXAMPLE 3 (Product obtained by freeze drying of Pantoprazole sodium sesquihydrate and sodium-hydroxide) particles/per vial $>= 10$ μm | EXAMPLE 4 (Product obtained by freeze drying of Pantoprazole sodium sesquihydrate and ethylenediamine tetraacetic acid disodium salt) particles/per vial $>= 10$ μm |
|---|---|---|---|
| 109 | 458 | 144 | 211 |

The invention being thus described, it will be obvious that the same may be varied in many ways. Such variations are not to be regarded as a departure from the spirit and scope of the invention and all such modifications are intended to be included within the scope of the following claims.

The invention claimed is:

1. Lyophilized preparation consisting of:
   (a) 5-difluoromethoxy-2-[(3,4-dimethoxy-2-pyridinyl)methylsulfinyl]-1H-benzimidazole (pantoprazole) or a solvate, hydrate, salt, hydrate of a salt or solvate of a salt thereof;
   (b) ethylenediamine tetraacetic acid and/or a suitable salt thereof, and
   (c) sodium hydroxide and/or sodium carbonate.

2. The preparation according to claim 1, wherein the pantoprazole is pantoprazole sodium.

3. The preparation according to claim 1, wherein the pantoprazole is pantoprazole sodium sesquihydrate.

4. The preparation according to claim 1, wherein the pantoprazole is pantoprazole magnesium.

5. The preparation according to claim 1, wherein the pantoprazole is pantoprazole magnesium dihydrate.

6. The preparation according to claim 1, wherein the pantoprazole is (−)-pantoprazole or a solvate, hydrate, salt, hydrate of a salt or solvate of a salt thereof.

7. The preparation according to claim 1, wherein the ethylenediamine tetraacetic acid is present as ethylenediamine tetraacetic acid disodium salt.

8. The preparation according to claim 2, wherein the ethylenediamine tetraacetic acid is present as ethylenediamine tetraacetic acid disodium salt.

9. The preparation according to claim 3, wherein the ethylenediamine tetraacetic acid is present as ethylenediamine tetraacetic acid disodium salt.

10. The preparation according to claim 4, wherein the ethylenediamine tetraacetic acid is present as ethylenediamine tetraacetic acid disodium salt.

11. The preparation according to claim 5, wherein the ethylenediamine tetraacetic acid is present as ethylenediamine tetraacetic acid disodium salt.

12. The preparation according to claim 6, wherein the ethylenediamine tetraacetic acid is present as ethylenediamine tetraacetic acid disodium salt.

13. The preparation according to claim 1, consisting of
   (a) Pantoprazole sodium;
   (b) ethylenediamine tetraacetic acid disodium salt; and
   (c) sodium hydroxide.

14. The preparation according to claim 1 consisting of:
   (a) Pantoprazole sodium sesquihydrate;
   (b) ethylenediamine tetraacetic acid disodium salt; and
   (c) sodium hydroxide.

* * * * *